United States Patent
Murphy et al.

Patent Number: 5,112,359
Date of Patent: May 12, 1992

[54] HAIR COLORANTS

[75] Inventors: Bryan P. Murphy, Monroe; Gabriella Wis-Surel, Milford, both of Conn.

[73] Assignee: Clairol, Inc., New York, N.Y.

[21] Appl. No.: 532,299

[22] Filed: Jun. 4, 1990

[51] Int. Cl.⁵ .............................................. A61K 7/13
[52] U.S. Cl. .................................... 8/405; 8/406; 8/425; 8/428; 8/429; 8/435; 424/70
[58] Field of Search ............... 8/428, 429, 435, 405, 8/406, 425; 424/70

[56] References Cited

U.S. PATENT DOCUMENTS

| | | | |
|---|---|---|---|
| 2,051,004 | 8/1936 | Koeberle et al. | 552/253 |
| 3,811,830 | 5/1974 | DeMarco | 8/428 |
| 4,602,913 | 7/1986 | Grollier | 8/405 |

FOREIGN PATENT DOCUMENTS

| | | |
|---|---|---|
| 0826479 | 1/1960 | United Kingdom. |
| 0918597 | 2/1963 | United Kingdom. |

Primary Examiner—A. Lionel Clingman
Assistant Examiner—William S. Parks

[57] ABSTRACT

Certain dispersant free substituted diaminoanthaquinone colorants are useful in hair dye compositions to more intensely color hair. Coloring kits, mousses, gels, and aerosols may contain the compositions.

13 Claims, No Drawings

HAIR COLORANTS

BACKGROUND

The use of various types of anthraquinones as colorants for keratinaceous substrates is known. However, the use of anthraquinones is complicated by the fact that most must be either (1) chemically modified and/or mixed with dispersants to make them useful in aqueous formulations or (2) heated to temperatures above 40° C. during coloring in order to produce the desired colors.

U.S. Pat. No. 2,051,004 discloses dispersion dyes whose structures are similar to those of applicants' colorants.

U. S. Pat. No. 3,368,942 shows the chemical modification of anthraquinones to render them water soluble, so that added dispersants and high temperatures need not be used to color human hair. Example 8 of the patent shows a hydroxyethane-substituted derivative.

Colour Index, 3rd ed.,vol. 4, p. 4539 discloses C.I. Disperse Blue 3. It is taught to be soluble in acetone, alcohol, benzene and Cellosolve, as well as slightly soluble in carbon tetrachloride. The principal component of C.I. Disperse Blue 3 (also called "Solvent Blue B" when in its dispersant-free form) is 1-methylamino-4-(2hydroxyethyl)-aminoanthraquinone.

Dispersants commonly added to dispersion, or disperse, dyes to render them dispersable in water-based solutions are alkylbenzene sulfonates or ethylene adducts of fatty acids or alcohols and the like. A partial list of useful dispersants is recited at col. 2, line 15+ of U.S. Pat. No.3,368,942. The use of these dispersants may lead to side reactions, resulting in unwanted impurities in the coloring formulations.

All disclosures referred to herein are hereby incorporated by reference.

THE INVENTION

It has been surprisingly discovered that keratin fibers can be colored to very intense shades via the use of compositions containing one or more dyes which are diaminoanthraquinones requiring no added dispersants and bearing certain substituents, but containing no water solubilizing groups.

In a preferred embodiment, an undispersed diaminoanthraquinone of the invention is mixed in an organic solvent, eg., diethylene glycol monomethylether, along with an amine alkalizer and other dyes and that combination is added to a 50°-80° C. thickened aqueous solution which contains fragrance and more amine alkalizer. Optional ingredients, such as cosmetic adjuvants and supplemental colorants, are then added. This mixture is maintained at high temperature to assure dissolution. After cooling to room temperature, it is applied to human hair.

Surprisingly, very intense colors are produced. In addition, and even more surprisingly, the anthraquinone dyes remain in solution on cooling and during product storage, so that equally intense dyeings are produced even months after manufacture.

ADVANTAGES

The coloring system of the invention has several advantages over the use of conventional dyeing systems.

First of all, the production of the anthraquinone dyes is easier and less expensive—in terms of both time and money—because no dispersing step is needed in its manufacture.

Second, the use of dispersants with some anthraquinones has led, in the past, to the production of unwanted color, eg., yellowish and dark or drab colors, on the dyed substrates. The fact that applicants' anthraquinone colorants are used with no added dispersants means that these undesirable color effects are substantially reduced.

Third, the use of raised temperatures during the coloring process is avoided. As was mentioned above, it has been necessary to heat anthraquinones to 40° to 60° C. in order to dye human hair with them. This necessitated the use of heating caps or other devices to color the hair.

Applicants' system avoids the use of raised temperatures during coloration. Room temperature coloring produces even dyeing of hair from light to dark shades, depending upon the nature and amount of the diaminoanthraquinone and/or any other colorant(s).

Fourth, when used in appropriate dye combinations, the nondispersed anthraquinones of the invention, which give blue to blue-green colors themselves, surprisingly yield black dyeouts having excellent depth or intensity of color.

The importance of this invention is highlighted by the fact that Disperse Blue 1 is presently no longer commercially available. Thus, the art has a great need for anthraquinones which produce intense black dyeouts in combination with other colorants. Applicants have not found it possible to obtain such colors using conventional dispersed anthraquinones alone.

These and other advantages of the invention will be apparent after a consideration of the following description and claims.

DESCRIPTION OF THE INVENTION

The invention is concerned with compositions and processes using same for coloring keratinaceous substrates. In addition, kits, gels, mousses and aerosols are contemplated.

Unless otherwise stated, all percentages stated herein are weight percentages, based on total composition weight.

The major constituents of the compositions of the invention are: (a) at least one anthraquinone colorant containing no dispersing aid (b) at least one organic carrier, (c) an alkalizer, and (d) water. Optionally, other colorants may be included in the compositions of the present invention. These colorants may contain dispersant(s).

Anthraquinones

The anthraquinone compounds useful in the invention are 1,4-diaminoanthraquinones bearing certain X and Y substituents on the two amino groups and, optionally, bearing substituents at other positions in the anthraquinone structure.

It is important to note that none of the substituents on the dye compounds of the invention render them salts. Thus no metal, sulfonate, carboxylic acid or other group which lends ionic character to the molecule is present.

The anthraquinones useful herein conform generally to formula I:

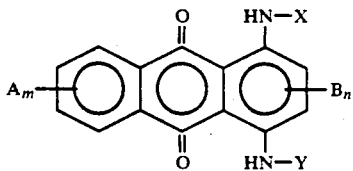

(I)

wherein

X is $C_{1-8}$ alkyl, $C_{1-8}$ haloalkyl or $C_{1-8}$ aminoalkyl;

Y is a hydroxy-substituted $C_{1-8}$ alkyl group, containing 1 to 4 hydroxyl groups and 0 to 4 amino groups, or a $C_{1-4}$ alkyl group;

A and B are independently selected from halo, X and Y;

m = 0–4; and n = 0–2.

Preferred compounds are those in which m and n are zero (0). Very preferred compounds are those in which m and n are zero, X is a $C_{1-8}$ alkyl group and Y is a monohydroxyalkyl group (ie., a group of the formula $C_aH_{2a}OH$) where $a = 1-8$. Most preferred are compounds wherein m = n = O, X is methyl or ethyl and Y is hydroxyethyl, hydroxymethyl or hydroxypropyl.

In the most preferred compounds, all alkyl groups are aliphatic, ie., normal, alkyl groups. One of the most preferred compounds of formula I is 1-methylamino-4-(2-hydroxyethyl)aminothraquinone.

By "halo" is meant chlorine, bromine, or fluorine residues, with chlorine and bromine preferred.

Compounds of formula I are commercially available. Many are disclosed in the Colour Index, such disclosures include methods for making same. The production of C.I. Disperse Blue 3 (whose principal constituent is 1-methylamino-4-(2-hydroxyethyl)aminoanthraquinone) is described in U.S. Pat. No. 2,051,004 and at Colour Index, 3rd ed., vol. 4, at page 4539. The condensation of 1-bromo-4-methylaminoanthraquinone with ethanolamine in the presence of copper acetate will yield this colorant.

While C.I. Disperse Blue 3 is known as a disperse dye (ie., suitable for use with dispersants or after chemical modification to render it water soluble), to the best of applicants' knowledge, it has not been heretofore employed without dispersants in aqueous formulations for coloring hair.

In the compositions and processes of the invention, this highly preferred colorant gives blue to blue-green dyeouts. When used with other, ie., conventional, dyes or colorants, it can produce ash blonde, golden brown or, surprisingly, intense black colors, as well as others.

Organic Carrier(s)

The dispersant free anthraquinones of the present invention require the presence of an organic carrier which insures their incorporation into the aqueous dye formulations. Suitable carriers include organic solvents, such as polyalkylene glycol monomethyl ethers, preferably diethylene glycol monomethylether, $C_{1-8}$ alcohols and glycols, preferably isopropyl alcohol, isobutyl alcohol, t-butyl alcohol, and benzyl alcohol, most preferably isopropyl alcohol, and the like. Mixtures are operable.

It is important to note that these carriers or solvents do not react with the anthraquinones. They merely assist their incorporation into the aqueous dye bases.

Although the anthraquinones of the present invention are dispersant free, the present invention contemplates the use, in the compositions of the invention, of other dyestuffs which can contain, as integral components, their own organic carriers or dispersants. Other materials which may be employed include anionic surfactants, such as sodium lauryl sulfate and oleic acids, and non-ionic surfactants, such as nonoxynol-9 and cetyl alcohol. Mixtures of surfactants can be used.

It is important to note that these carriers or solvents do not react with the anthraquinones. They merely assist in its solution into the water in the presence of the other ingredients in the hair coloring composition.

Alkalizer(s)

The compositions contain at least one alkalizing agent which is preferably an organic amine base. pH values of about 8 to about 11 are typical.

Suitable bases include monoethanolamine, diethanolamine, triethanolamine and the like. 2-amino-2-methylpropanol is preferred. Mixtures are operable.

Other Ingredients

The coloring formulations of the invention may contain a wide variety of additives. In addition to suitable quantities of auxiliary and/or primary dyes, they may also contain dye assistants, color modulators, thickeners, propellants, foaming agents, perfumes, stabilizers, cosmetic agents, flow control enhancers, eg., thinners, and surfacants and/or solvents for other dyes, etc. Suitable amounts of any or all of these are contemplated. The table below sets out useful quantity ranges.

When the dispersant-free anthraquinones are supplemented by other colorants, such colorants are generally of the nitrophenol, nitroaniline, nitrophenylene diamine or azo type. Dispersant-containing anthraquinones may also be added. Oxidative colorants may be employed.

When a gel or mousse is desired, suitable thickeners include, but are not limited, to hydroxypropylcellulose, polyacrylic acid and the like. Mixtures are operable.

When an aerosol preparation is wanted, suitable quantities of propellants, such as $CO_2$, $N_2O$, isobutane and the like are useful. Foaming agents, such as cetyl alcohol and the like, can also be employed. Mixtures are contemplated.

By "dispersants" applicants mean wetting or dispersing agents conventionally mixed with dyestuffs to form a powder or paste prior to formulating same into a hair coloring preparation.

Substrates

"Human hair" is mentioned throughout this discussion as a suitable substrate. It should be noted, however, that a wide variety of keratinaceous and proteinaceous substrates can be dyed using the invention. Hair growing on a human head, ie., "living" human hair, is preferred. In addition, live animal hair is a possible substrate.

Forms The compositions of the invention are generally of liquid character. However, they may also be semi-liquid or gel-like. Accordingly, mousses and gels are contemplated. Aerosol foams, such as those produced using one or more propellants and/or foaming agents, are also contemplated. Kits which contain the coloring formulations of the invention in one component and suitable catalysts, modulators, fixatives, etc. in one or more other(s) are also contemplated.

Amounts of Ingredients

The ingredients described herein will generally be used in coloring formulations in the amounts given in the table below.

TABLE

| AMOUNTS OF INGREDIENTS IN COMPOSITIONS OF THE INVENTION* | | | |
|---|---|---|---|
| | Broad Range | Preferred Range | Most Preferred Range |
| Anthraquinones | 0.001–4.0 | 0.01–1.0 | 0.03–0.7 |
| Organic carrier | 0.5–50 | 1–30 | 1–30 |
| Alkalizer | 0–20 | 0–10 | 0–10 |
| Auxiliary/Primary Colorants: | 0–20 | 0.001–8 | 0.01–5 |
| Other Ingredients | 0–90 | 0–70 | 0–60 |
| Water | q.s. to 100% | q.s. to 100% | q.s. to 100% |

*The total of all percentages for any one formulation will be 100%.

Preparation of the Composition

Typically, the ingredients are combined in the following sequence:
1) Anthraquinones and other colorants are mixed with carriers and solubilizing agents;
2) These are added to a premix of solubilized thickener, alkalizer and water;
3) Fragrance and other optional ingredients are added. Heat may be applied during one or both of steps 1) and 2).

Mixing temperatures of about 25° C. to about 80° C. are used. Preferred temperatures are about 50° to about 70° C. The composition is cooled to room temperature before use.

Dyeing Procedure

Typically, the final hair coloring formulation is contacted with hair or other substrate for about 5 to 60 minutes preferably about 10 to about 30 minutes. Following dye contact, the substrate is rinsed and/or shampooed to remove the formulation. Lightening/modulating steps are optional and may be carried out before or after the dyeing procedure, preferably before.

EXAMPLES

The following examples serve to illustrate the invention.

EXAMPLE 1

A mixture of 50 g of diethylene glycol monomethyl ether, 14.7 g of PEG-50 tallow amide, 14.7 g of lauramide DEA, 2.45 g of butylated hydroxytoluene, 19.6 g of oleic acid, 8.9 g of diethanolamine, 0.2 g of erythorbic acid, 0.16 g of Solvent Blue B, 0.15 g of HC Orange 1, 0.2 g of Disperse Black 9, 0.2 g of HC red 3, 0.28 g of HC Yellow 2, 0.42 g of HC Yellow 4, and 0.8 g of HC Blue 2 was heated to 60° C. When dissolution was complete, this mixture was added to a thickened solution of 11.3 g of hydroxyethylcellulose, 700 g of de-ionized water, and 1.1 g of diethanolamine at 60° C. When a homogeneous mixture results, water is added to bring the total weight of the formulation to 1 kg. Hair is dyed ash blonde with this formulation.

EXAMPLE 2

A mixture of 50 g of diethylene glycol monomethyl ether, 14.7 g of PEG-50 tallow amide, 14.7 g of lauramide DEA, 2.45 g of butylated hydroxytoluene, 19.6 g of oleic acid, 8.9 g of diethanolamine, 0.2 g of erythorbic acid, 1.3 g of Disperse Black 9, 1.8 g of Acid Orange 3, 2.2 g of HC Red 3, 3.3 g of HC Yellow 2, 1.5 g of Disperse Violet 1, 1.6 g of HC Yellow 4, 4.5 g of Solvent Blue B, and 11.0 g of HC Blue 2 was heated to 60° C. When dissolution was complete, this mixture was added to a thickened solution of 11.3 g of hydroxyethylcellulose, 700 g of de-ionized water, 1.2 g of fragrance, and 1.1 g of diethanolamine of 60° C. When a homogeneous mixture results, water is added to bring the total weight of the formulation to 1 kg. Hair is dyed dark golden brown with this formulation.

EXAMPLE 3

A mixture of 73.5 g of isopropyl alcohol, 14.7 g of PEG-50 tallow amide, 14.7 g of lauramide DEA, 4.5 of citric acid, 27 g of diethanolamine, 26 g of lauramide DEA, 2.45 g of butylated hydroxytoluene, 1.0 g of Solvent Blue B, 0.6 g of Disperse Black 9, 0.1 g of HC Red 3, 0.2 g of HC Yellow 2, 0.6 g of Acid Orange 3, 7.4 g of Disperse Violet, 2.1 g of HC Yellow 3, 0.7 g of Disperse Blue 3, and 7.1 g of HC Blue 2 was heated to 60° C. When dissolution was complete, this mixture was added to a thickened solution of 9.3 g of hydroxyethylcellulose, 700 g of de-ionized water, and 3.1 g of diethanolamine at 60° C. When a homogeneous mixture results, water is added to bring the total weight of the formulation to 1 kg. Surprisingly, the hair swatch dyed with this composition was dyed an intense natural black color.

EXAMPLE 4

For comparative purposes, Example 3 was repeated, except that the Solvent Blue B was replaced by an additional 2.0 g of Disperse Blue 3. (Disperse Blue 3 contains 50% lignin sulfonate dispersant and 50% Solvent Blue B.) The hair swatch dyed with this composition was dyed a very weak grey-black color.

Thus, it has been surprisingly and unexpectedly found that the use of dispersant-free anthraquinones in dye mixtures yields dyeings which are more intense than those attained in the absence of the dispersant-free anthraquinones. Example 3 wherein dispersant-free Solvent Blue B and Disperse Blue 3 were used, along with other colorants, gave an intense black dyeout on human hair. Example 4, in which no dispersant-free dye was used and Disperse Blue 3 was used, gave a faded gray-black dyeout.

Reasonable variations, such as those which would occur to a skilled artisan, can be made herein without departing from the scope of the invention.

We claim:
1. In an aqueous composition for coloring keratinaceous substrates, said composition containing (a) a mixture of two or more dyestuffs, one of which being a substituted 1,4-diaminoanthriaquinone of formula I:

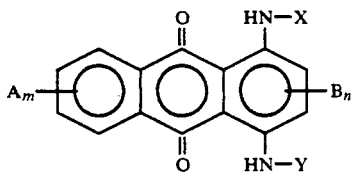

wherein

X is $C_{1-8}$ alkyl, $C_{1-8}$ haloalkyl or $C_{1-8}$ aminoalkyl;

Y is a hydroxy-substituted $C_{1-8}$ alkyl group containing 1 to 4 hydroxyl groups and 0 to 4 amino groups, or a $C_{1-4}$ alkyl groups;

A and B are independently selected from halo, X and Y;

m = 0–4; and n = 0–2;

(b) an organic carrier for the dyestuffs, and (c) water, wherein the improvement comprises the compound of formula I being in a dispersant-free form and, whereby, upon dyeing, the keratinaceous substrates are dyed more intensely.

2. The composition of claim 1 wherein m and n are both zero, X is an alkyl group and Y is a $C_aH_{2a}OH$ group.

3. The composition of claim 2 wherein (a) is 1-methylamino-4-(2-hydroxymethyl)aminoanthraquinone.

4. A process for coloring a keratinaceous substrate comprising the step of contacting the substrate with an aqueous composition which contains:

(a) at least one dispersant free first colorant of formula I:

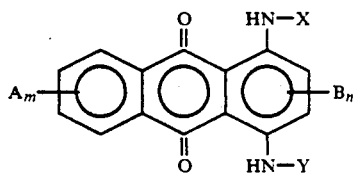

wherein

X is $C_{1-8}$ alkyl, $C_{1-8}$ haloalkyl or $C_{1-8}$ aminoalkyl;

Y is a hydroxy-substituted $C_{1-8}$ alkyl group containing 1 to 4 hydroxyl groups and 0 to 4 amino groups, or a $C_{1-4}$ alkyl group;

A and B are independently selected from halo, X and Y;

m = 0–4; and n = 0–2;

(b) at least one second colorant optionally containing a dispersing agent; and (c) an organic carrier for the first and second colorants.

5. The process of claim 4 wherein m and n are both zero, X is an alkyl group and Y is a $C_aH_{2a}OH$ group.

6. The process of claim 12 wherein (a) is 1-methylamino-4-(2-hydroxyethyl)-aminoanthraquinone.

7. A hair coloring kit containing, in one component, the composition of claim 1.

8. A hair coloring mousse containing the composition of claim 1.

9. A hair coloring gel containing the composition of claim 1.

10. An aerosol hair coloring formulation containing the composition of claim 1.

11. A method of enhancing the depth of color imparted to a dyed keratinaceous substrate comprising contacting the substrate with a dye composition made by mixing a dispersant-free anthraquinone dye of formula I with one or more conventional dyes, said mixing taking place in the presence of a carrier for the anthraquinone dye, wherein formula I is:

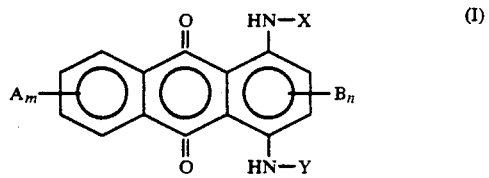

wherein

X is $C_{1-8}$ alkyl, $C_{1-8}$ haloalkyl or $C_{1-8}$ aminoalkyl;

Y is a hydroxy-substituted $C_{1-8}$ alkyl group, containing 1 to 4 hydroxyl groups and 0 to 4 amino or $C_{1-4}$ alkyl groups;

A and B are independently selected from halo, X and Y;

m = 0–4; and n = 0–2.

12. The method of claim 11 wherein m and n are both zero, X is an alkyl group and Y is a $C_aH_{2a}OH$ group.

13. The method of claim 12 wherein the anthraquinone dye is 1-methylamino-4-(2-hydroxyethyl)aminoanthraquinone.

* * * * *